United States Patent [19]

Gold

[11] 4,327,747
[45] May 4, 1982

[54] TERMINAL ASSEMBLY FOR A CARBON FIBER IMPLANTABLE LEAD

[75] Inventor: Philip Gold, Pompano Beach, Fla.

[73] Assignee: Cordis Corporation, Miami, Fla.

[21] Appl. No.: 189,125

[22] Filed: Sep. 22, 1980

[51] Int. Cl.$^3$ .............................................. A61N 1/04
[52] U.S. Cl. ................................. 128/784; 128/419 P
[58] Field of Search ..................... 128/419 P, 784, 785, 128/786

[56] References Cited

U.S. PATENT DOCUMENTS

| | | | |
|---|---|---|---|
| 3,437,091 | 4/1969 | Jerushalmi et al. | 128/786 |
| 3,769,984 | 11/1973 | Muench | 128/491 P |
| 4,198,991 | 4/1980 | Harris | 128/419 P |
| 4,258,725 | 3/1981 | O'Neill | 128/419 P |
| 4,273,137 | 6/1981 | Pravoverov et al. | 128/784 |

FOREIGN PATENT DOCUMENTS 2810004  9/1978  Fed. Rep. of Germany ...... 128/786

Primary Examiner—William E. Kamm
Attorney, Agent, or Firm—Kenway & Jenney

[57] ABSTRACT

A termination for a carbon fiber implantable lead. A terminal assembly includes a hollow terminal member having lateral ports through which carbon fiber bundles pass. Exposed tips of the carbon fiber bundles are folded back and held against the exterior surface of the terminal member by a housing member. The housing member frictionally engages the exposed fiber tips. A stylet entry guide member is frictionally engaged with the interior of the end of the terminal member. One end of the guide member is coupled to a stylet tube which passes through the terminal member and the lead. This configuration provides a good electrical coupling between the terminal member and the carbon fiber bundles, as well as provides an axial passage through which a stylet may be inserted.

6 Claims, 10 Drawing Figures

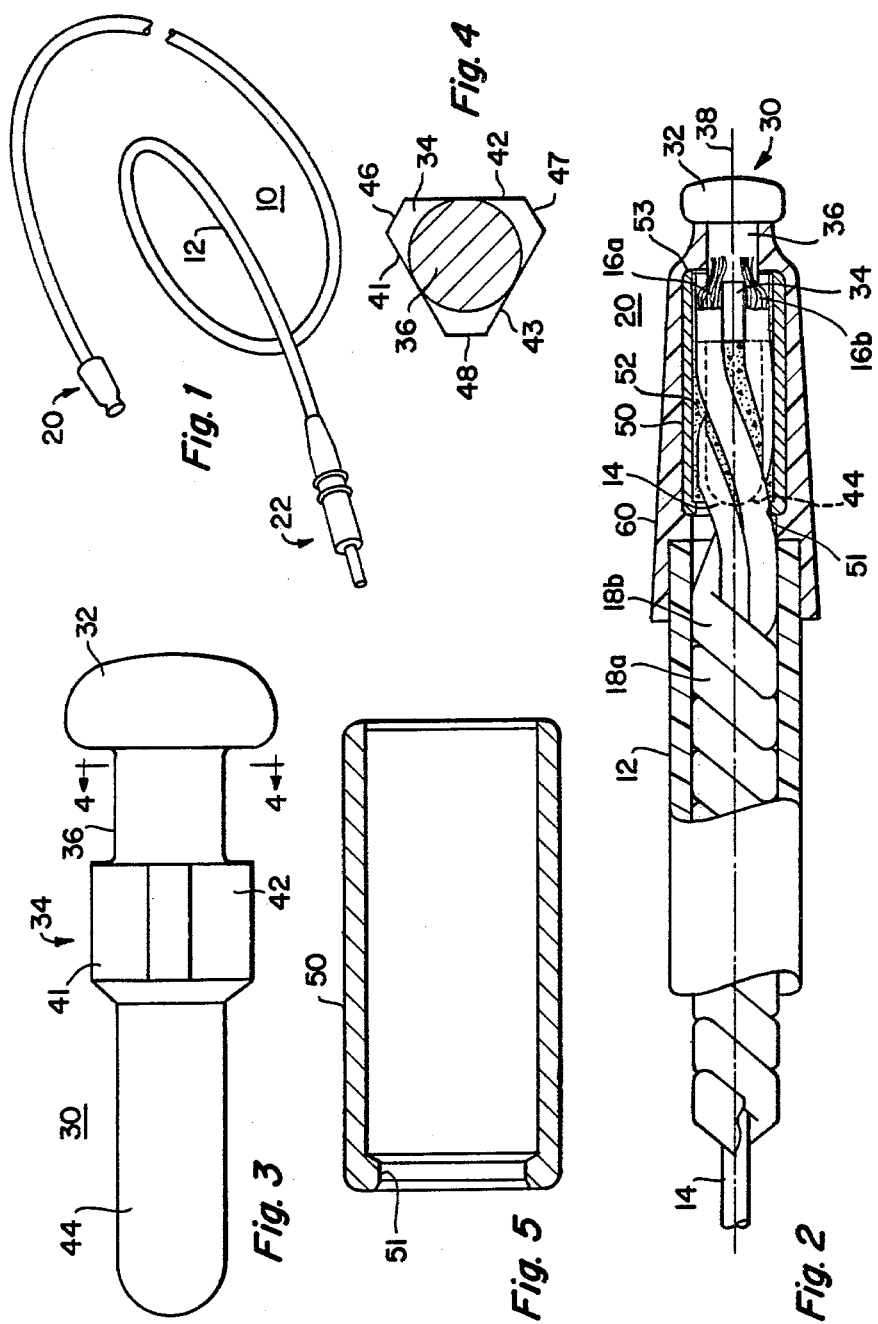

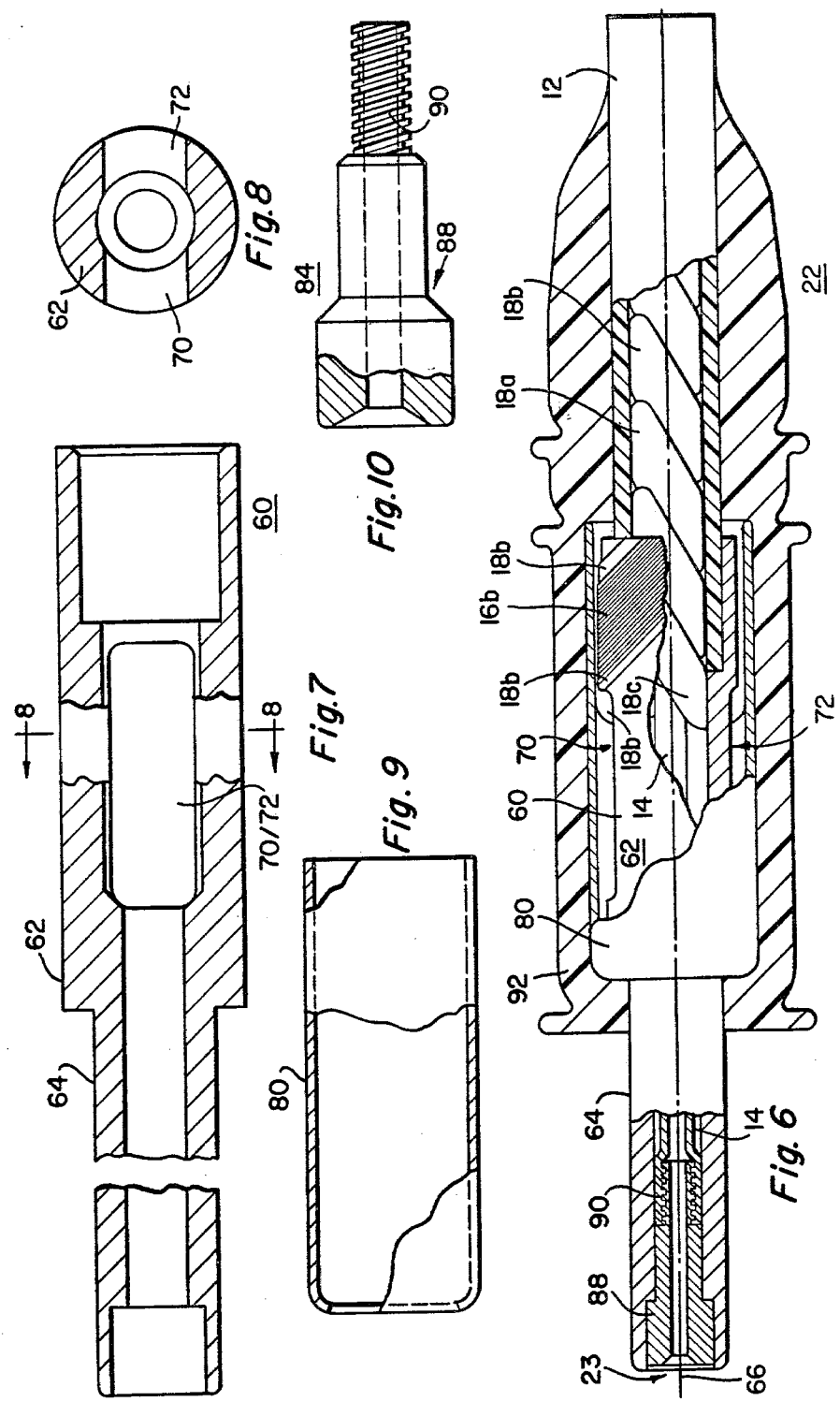

TERMINAL ASSEMBLY FOR A CARBON FIBER IMPLANTABLE LEAD

REFERENCE TO RELATED APPLICATION

The subject matter of this application is related to that of U.S. Pat. No. 4,198,991 entitled "Cardiac Pacer Lead". The patent is incorporated herein by reference.

BACKGROUND OF THE INVENTION

The present invention is in the field of implantable leads, more particularly, terminations for carbon fiber implantable leads.

There have been increasing applications in recent years for implantable electrical leads for coupling electrical signals to and from or between various points in human or animal bodies. The incorporated reference patent describes one such application, that is, cardiac pacing by means of an implantable stimulator. As particularly pointed out in that reference, such implantable leads are typically subject to continuous flexing which may result from heartbeat, breathing or other body movements. Consequently, the leads are designed to be both pliant and fatigue-resistant.

The incorporated reference patent discloses a carbon fiber lead which is particularly well-suited for cardiac pacing and which is highly pliant and fatigue-resistant.

One of the difficulties with implantable carbon fiber leads in the prior art is the coupling of a termination assembly to the carbon fiber leads at both the tip end (which is implantable within a patient), and the terminal end (which is the end to be coupled to either sensor instrumentation or signal generating instrumentation). In typical prior art carbon fiber leads, particularly those having bundles of carbon fibers, or yarn, sheathed in tetrafluoroethylene, there has proven to be a substantial problem due to the inability to maintain a long life mechanical coupling between the terminations and the sheathing material.

It is an object of the present invention to provide an improved terminal assembly for carbon fiber implantable leads.

It is yet another object to provide an improved terminal assembly for a carbon fiber implantable lead which maintains good electrical contact between an electrical coupling member and the internal carbon fiber bundles, while maintaining a relatively good mechanical coupling between the termination assembly and the lead.

SUMMARY OF THE INVENTION

Briefly, the present invention includes a terminal assembly for an implantable carbon fiber lead which has an outer cover disposed about a stylet tube and one or more carbon fiber bundles. Each carbon fiber bundle has an insulating outer sheath (for example, made of a fluorocarbon material, such as polytetrafluoroethylene, PTFE) and an exposed carbon fiber tip at the end of the lead to be coupled. In one form of the invention, the outer sheath is split at its end and the fibers from within that end pass through the split. The fibers passing through that split, including their lateral surfaces form the exposed tip. The terminal assembly includes a hollow, cylindrical termination member. A first end of the terminal member is positioned about the coupling end of the stylet tube, i.e. the end of stylet tube at the end of the lead to be coupled. The second end of the terminal member is positioned about a portion of the stylet tube near that end and about portions of the carbon fiber bundles. The second end of the terminal member has one or more ports in its lateral surface. Each of those ports is adapted for guiding a portion of an associated one of the carbon fiber bundles near its exposed tip and at least a portion of the outer sheathing from that tip from the region inside the second end of the terminal member to the region outside that second end. In the preferred form, the exposed tips and associated sheathing are folded back over the second end of the terminal member, with the exposed tips outermost.

An electrically conductive terminal housing member is positioned about the second end of the terminal member so that the exposed tips and sheathing are sandwiched between the inner surface of the housing and the outer surface of the second end of the terminal member.

In some forms of the invention, an electrically conductive adhesive cements the exposed tips and associated portion of the outer sheathing (that extend through the ports) to the outer surface of the second end of the terminal member and the housing.

The terminal assembly further includes a stylet entry guide member which has a hollow body portion connected to a coaxial hollow head portion. The body portion has a threaded outer surface which extends into and frictionally engages the coupling end of the stylet tube. The head portion of the stylet entry guide member is positioned within the first end of the terminal member so that its outer surface frictionally engages the inner surface of that end of the terminal member.

In various forms of the invention, a molded insulating member may be disposed about the outer surface of the terminal housing member.

With this configuration, a terminal assembly is provided for the carbon fiber lead which may be adapted for coupling to conventional electronic sensor or signalling devices, such as an implantable cardiac pacer. Moreover, the terminal assembly is particularly adapted for the insertion of a stylet into the stylet entry guide member, and the stylet tube, at the terminal end of the lead, for use in positioning the lead during implantation in a patient. The mechanical interaction of the carbon fiber bundle sheaths with the ports of the terminal member and the terminal housing member, provide a connection of the terminal assembly to the carbon fiber lead in a manner minimizing slipping and dislodging, and thereby providing a relatively long life assembly.

BRIEF DESCRIPTION OF THE DRAWINGS

The foregoing and other objects of this invention, the various features thereof, as well as the invention itself, may be more fully understood from the following description, when read together with the accompanying drawings in which:

FIG. 1 shows an implantable carbon fiber lead embodying the present invention;

FIG. 2 shows a cutaway view of the tip assembly of the lead of FIG. 1;

FIG. 3 shows the electrode of the tip assembly of FIGS. 1 and 2;

FIG. 4 shows a section of the electrode of FIG. 3 along lines 4—4;

FIG. 5 shows the electrode housing of the tip assembly of FIGS. 1 and 2;

FIG. 6 shows a cutaway view of the terminal assembly of the lead of FIG. 1;

FIG. 7 shows, in section, the terminal member of the terminal assembly of FIGS. 1 and 6;

FIG. 8 shows a section of the terminal member of FIG. 7 along lines 8—8;

FIG. 9 shows a cutaway view of the housing member of the terminal assembly of FIGS. 1 and 6; and FIG. 10 shows a cutaway view of the guide member of the terminal assembly of FIGS. 1 and 6.

DESCRIPTION OF THE PREFERRED EMBODIMENT

FIGS. 1-10 show an implantable carbon fiber lead 10 embodying the present invention. Lead 10 generally includes an outer cover 12 (e.g. made of a suitable material such as polyurethane or silastic) which encloses a stylet tube 14 and two carbon fiber bundles 16a and 16b. Each of bundles 16a and 16b has an insulating sheath (18a and 18b, respectively) and has an exposed carbon fiber tip at each end. In the present embodiment, the sheathed carbon fiber bundles 16a and 16b are helically wound around the exterior of the stylet guide 14. In this embodiment, the sheaths 18a and 18b, and stylet tube 14, are made of a fluorocarbon material, such as polytetrafluoroethylene (PTFE).

The lead 10 also includes a tip assembly 20 at its distal end which provides an exterior electrically conductive surface which is coupled to the carbon fiber bundles passing within the cover 12. At the proximal end of lead 10, a terminal assembly 22 provides a conductive electrical termination to the carbon fiber bundles. This termination is suitable for coupling to conventional electronic sensor or signalling devices, such as an implantable cardiac pacer. In addition, the terminal assembly 22 includes a central opening 23 which is coupled to the interior of stylet tube 14. This opening 23 is particularly adapted for permitting the insertion of a stylet into the stylet tube 14.

FIGS. 2-5 show the distal end tip assembly 20 and its component parts in detail. More particularly, FIG. 2 shows a cutaway view of the tip assembly 20. Assembly 20 includes an electrode 30 (shown in detail in FIGS. 3 and 4) which has a tip portion 32 at one end, a contact portion 34, a neck portion 36 interconnecting the contact portion 34 and the tip portion 32 along a central axis 38, and a post portion 44 at its other end. The post portion 44 extends along the central axis 38 away from the contact portion 34. In the present embodiment, the neck portion 36 has a relatively small cross-sectional area relative to the adjacent sections of the tip 32 and contact portion 34. The contact portion 34 includes three substantially planar lateral contact surfaces 41, 42 and 43. In alternate embodiments, differing numbers of contact surfaces may be used. As shown in FIG. 4, the contact portion 34 includes regions 46, 47 and 48 which respectively lie between the planar surfaces 41, 42 and 43.

An electrically conductive hollow electrode housing member 50 is positioned about the contact portion 34 and the post portion 44 of the electrode 30. Electrode housing member 50 includes a lip 51 at one end.

In the assembled form, the exposed tips of carbon fiber bundles 16a and 16b as well as the end stylet tube 14 extend to respective ones of the contact surfaces 41–43, and beyond to the neck portion 36. The exposed tips are cemented to a respective one of the surfaces 41–43, as well as to the inside surface of housing member 50. The adhesive used for cementing the carbon fiber tips to their respective contact surfaces is electrically conductive, such as a silver or platinum-loaded epoxy material. In addition, the end of housing member 50 is crimped (at 53) to mechanically secure, as well as electrically couple, the carbon fiber tips and end of tube 14 to the electrode 30. The crimp 53 of housing 50 at neck portion 36 forces the lip 51 of housing 50 to cooperatively interact with the post portion 44 to mechanically secure the sheathing from the fiber bundles and the tube 14 against electrode 30.

In the present embodiment, a conductive potting 52 is also positioned within the housing 50 in contact with electrode 30. In addition, the assembly 20 includes an insulating member 60 which may be of silastic or polyurethane or other suitable moldable material, which is positioned about the housing member 50 and overlaps the cover 12 and the neck portion of electrode 30, bonding and moisture sealing the entire tip and lead body assembly.

With this configuration, the exposed tips of the two carbon fiber bundles 16a and 16b are cemented to the contact surfaces of the electrode 32. The electrically conductive adhesive on tips of bundles 16a and 16b, and the crimp coupling at neck 36 provide electrical contact, as well as mechanical coupling, between the fiber bundles and the electrode 30. Moreover, the conductive potting 52 within the electrode housing 50 further insures good electrical contact between the carbon fiber bundles and the electrode 30. The frictional engagement of the housing 50 to the portions 46, 47 and 48 of contact portion 34, together with the potting 52, as well as frictional engagement of tip 51 and post 44 with the bundles 16a and 16b insure good mechanical contact between the carbon fiber bundles within the cover 12 and the electrode tip 30.

FIGS. 6-10 show the proximal end terminal assembly 22 and its component parts in detail. More particularly, FIG. 6 shows a cutaway view of the terminal assembly 22. The assembly 22 includes a terminal member 60 (shown in detail in FIGS. 7 and 8) which includes two connected hollow, cylindrical ends 62 and 64 which are coaxial about an axis. In the preferred embodiment, the first end 64 has a relatively small outer diameter compared with the second end 62. In other forms of the invention, both ends 62 and 64 may have the same diameter.

In the terminal assembly 22, the ends of sheaths 18a and 18b near the terminal end of 10 are split and the fibers at that end pass through the split to form an exposed tip. The first end 64 is positioned about one end of the stylet tube 14, and the second end 62 is in part positioned about a portion of the stylet tube 14 as well as portions of the carbon fiber bundles 16a and 16b within their sheaths 18a and 18b, respectively. The terminal member end 62 includes two ports denoted by reference designation 70 and 72. Each of ports 70 and 72 is adapted to guide one of the carbon fiber bundles 16a and 16b from its respective split portion of sheathing 18a and 18b from the region interior to terminal member end 62 to the region exterior to that end 62. The exposed tips and sheathing are folded back against the outer surface of end 62, with the fiber bundles outermost.

The terminal assembly 22 further includes an electrically conductive hollow housing member 80, shown in detail in FIG. 9. The housing member 80 is positioned about the cylindrical portion 62 so that the inner surface of housing 80 sandwiches the exposed tips and associated sheathing between that inner surface and the outer surface of terminal member end 62. The housing member 80 may be mechanically coupled, or secured, to terminal member 60, for example, by a threaded coupling, crimp (particularly in the region of ports 70 and 72), or spot weld. In some forms of the invention, an electrically conductive adhesive cements those exposed tips and shething between the housing member 80 and end 62. In alternate embodiments, a conductive potting may be used within housing 80 and end 62 to further insure good electrical contact between the carbon fiber bundles and terminal member 60.

The terminal assembly 22 further includes a stylet entry guide member 84 having a hollow end portion 88 coupled to a coaxial, hollow body portion 90. Guide member 84 is positioned within the terminal member end 64 of terminal member 60 so that the outer surface of guide member 84 frictionally engages the inner surface of end 64. The outer surface of part of the body portion 90 is threaded and is frictionally engaged with the inner surface of the stylet tube 14. In the present embodiment, a molded insulating member 92 is positioned about a portion of the cylindrical portion 64 as well as the housing member 80 and the end of outer sheathing 12 forming a moisture seal. As shown, member 92 is a seal particularly adapted for use with an implanted cardiac pacemaker.

With this configuration, the exposed tips of the two carbon fiber bundles 16a and 16b are mechanically and electrically coupled to the terminal assembly 22. The electrically conductive adhesive on the tips of bundles 16a and 16b provides additional mechanical and electrical contact between the fiber bundles and terminal member 60. The frictional engagement of the housing 80 to the fiber tips and to the sheathing insures good mechanical contact between the carbon fiber bundles within the cover 12 and the terminal member 60.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A terminal assembly for an implantable carbon fiber lead having an outer cover disposed about a stylet tube and one or more carbon fiber bundles, each of said bundles having an insulating outer sheath and having an exposed carbon fiber tip at the end to be coupled, comprising:

A. a terminal member having a hollow cylindrical portion, the first end of said cylindrical portion being disposed about and substantially coaxial with one end of said stylet tube, said one end being at the coupling end of said lead, and the second end of said cylindrical portion being disposed about a portion of said stylet tube near said one end and about portions of said carbon fiber bundles, said second end having one or more ports in its lateral surface, wherein a portion of at least one of said carbon fiber bundles near its exposed tip and at least a portion of the sheathing of said bundle is guided through an associated one of said ports from the region inside said second end to the region outside said second end to the region outside said second end, and folded back against the outer surface of said second end, B. a hollow cylindrical housing member disposed about said second end wherein the inner surface of said terminal housing member cylindrical portion frictionally engages the exposed tips and associated sheathing of the carbon fiber bundles which extend through said ports, and C. means for securing said housing member to said terminal member.

2. A terminal assembly according to claim 1 further comprising a stylet entry guide member having a hollow cylindrical end connected to a coaxial hollow cylindrical body member, said body member including a threaded outer surface extending into and frictionally engaging the end of said stylet tube, said end member having its outer surface frictionally engaging the inner surface of the end of said first end of said cylindrical portion.

3. A terminal assembly according to claims 1 or 2 further comprising an electrically conductive adhesive means for cementing said exposed tips and associated sheathing between the outer surface of said second end and the inner surface of said terminal housing member.

4. A termination assembly according to claims 1 or 2 wherein said fiber bundle insulating sheath is a fluorocarbon material.

5. A termination assembly according to claims 1 or 2 further comprising an insulating member disposed about said housing member.

6. A termination assembly according to claim 2 wherein said stylet tube is a fluorocarbon material.

* * * * *